United States Patent [19]
Weisburg et al.

[11] Patent Number: 5,464,743
[45] Date of Patent: Nov. 7, 1995

[54] NUCLEIC ACID PROBES AND METHODS FOR DETECTING CRYPTOCOCCUS NEOFORMANS

[75] Inventors: William G. Weisburg, Milford; Susan M. Barns, Hopkinton, both of Mass.

[73] Assignee: Amoco Corporation, Naperville, Ill.

[21] Appl. No.: 908,849

[22] Filed: Jul. 1, 1992

Related U.S. Application Data

[63] Continuation of Ser. No. 795,112, Nov. 20, 1991, abandoned, which is a continuation of Ser. No. 420,578, Oct. 12, 1989, abandoned.

[51] Int. Cl.$^6$ .............................. C12Q 1/68; C07H 21/04; C12P 19/34
[52] U.S. Cl. ...................... 435/6; 536/24.32; 536/24.33; 935/77; 935/78; 435/91.2
[58] Field of Search ............... 536/23.1, 24.32, 536/24.33; 435/6, 91.2; 935/77, 78, 3, 8; 436/501

[56] References Cited

FOREIGN PATENT DOCUMENTS 8803957  6/1988  WIPO .

OTHER PUBLICATIONS

Biosis Abstract No. 88130563, Restrepo et al, J. Bacteriol., 171(10), 1989 pp. 5596–5600.
Forman et al., Abstract of Mol. Cell. Biol., 9, 1989, pp. 1137–1147.
Japanese Patent No. 62104583, Abstract, May 15, 1987.
Japanese Patent No. 62104582, Abstract, May 15, 1987.
European Patent No. 289478, Abstract, Nov. 2, 1988.
Aulakh et al., Int. J. Syst. Bacteriol., Jan. 1981, pp. 97–103.
Restrepo et al. (Oct. 1989) & Bacteriol. 171(10):5596–5600.
Medlin et al. (1988) Gene 71:491–499.
Gueho et al. (1989) System. Appl. Microbiol. 12:230–236.

Primary Examiner—Margaret Parr
Assistant Examiner—Lisa Arthur
Attorney, Agent, or Firm—Norval B. Galloway

[57] ABSTRACT

Nucleic acid probes are described for detecting yeasts capable of causing cryptococcosis, specifically *Cryptococcus neoformans*. The preferred probes are complementary to the ribosomal ribonucleic acid sequences unique to *Cryptococcus neoformans*, and as such can detect the rRNA, rDNA, or polymerase chain reaction amplification products of these genes. The detection of the etiological agent of human cryptococcosis, and tests for making a clinical diagnosis of this disease utilizing specific rRNA or rDNA probes are now possible.

8 Claims, 1 Drawing Sheet

NUCLEIC ACID PROBES AND METHODS FOR DETECTING CRYPTOCOCCUS NEOFORMANS

This is a continuation of application Ser. No. 07/795,112 filed Nov. 20, 1991, now abandoned, which is a continuation of 07/420,578 filed Oct. 12, 1989.

FIELD OF THE INVENTION

This invention relates to detection of fungi belonging to the species *Cryptococcus neoformans*. More specifically, it provides nucleic acid probes and compositions along with methods for their use for the specific detection of cryptococcosis causing fungi.

BACKGROUND OF THE INVENTION

*Cryptococcus neoformans* is the etiological agent of human cryptococcosis. Cryptococcosis, as described in one textbook (Rippon, J. W., Medical Mycology, Saunders Co., Philadelphia, 1988), is a chronic, subacute or acute pulmonary, systemic, or meningitic yeast infection, generally beginning with a pulmonary infection. Its most serious clinical manifestation is in the central nervous system where it is the most prevalent agent of fungemic meningitis. Prior to the advent of amphotericin-B drug therapy, it was almost always fatal.

*Cryptococcus neoformans*, also known as *Filobasidiella neoformans*, is considered an opportunistic pathogen. The immune-compromised population, including AIDS/HIV infected individuals and cancer patients, is particularly susceptible to cryptococcosis. The organism is widely distributed in nature. The common pigeon, *Columba livia*, is a reservoir for cryptococcus. *Cryptococcus neoformans* can be recovered in large numbers from accumulated pigeon droppings in the birds' roosts.

Cryptococcus (also synonymous with the genus Filobasidiella) is a genus of Basidiomycetous yeasts. As such, herein they rill be referred to as "yeasts", "fungi", or "cryptococci". (Candida yeasts—the most clinically prevalent genus—are Ascomycetous yeasts.) There are several species of Cryptococcus; only *C. neoformans* is recognized as pathogenic. *Cryptococcus albidus* and *C. laurentii* are isolated from human clinical samples, but are not considered the causative agents of morbidity. Within *C. neoformans*, there are four known serotypes; A, B, C, and D. Serotype A is the most common pathogenic biotype.

Current diagnostic assays employ either India ink staining of clinical samples for microscope evaluation, or latex agglutination assays. Both technologies require high numbers of yeast cells in the sample.

It is an aspect of the present invention to provide nucleic acid probes which are specific for yeasts capable of causing cryptococcosis and related morbidity, particularly specific for the detection of *Cryptococcus neoformans*.

It is another aspect to provide probes which may be used in a variety of assay systems which avoid many of the disadvantages of the currently used detection methods.

It is still another aspect of the present invention to provide probes which can hybridize to target regions which can be rendered accessible to probes under normal assay conditions.

While Kohne at el. (Biophysical Journal 8:1104–1118, 1968) discuss one method for preparing probes to rRNA sequences, they do not provide the teaching necessary to sake *Cryptococcus neoformans* specific probes or any other probes to detect fungi.

Pace and Campbell (Journal of Bacteriology 107:543–547, 1971) discuss the homology of ribosomal ribonucleic acids from diverse bacterial species and a hybridization method for quantitating such homology levels. Similarly, Sogin, Sogin and Woese (Journal of Molecular Evolution 1:173–184, 1972) discuss the theoretical and practical aspects of using primary structural characterization of different ribosomal RNA molecules for evaluating phylogenetic relationships. Fox, Pechman and Woese (International Journal of Systematic Bacteriology 27:44–57, 1977) discuss the comparative cataloging of 16S ribosomal RNAs as an approach to prokaryotic systematics. These references, however, fail to relieve the deficiency of Kohne's teaching with respect to fungi, and in particular, do not provide specific probes useful in assays for detecting cryptococcosis or its etiological agent, *Cryptococcus neoformans*.

Ribosomes are of profound importance to all organisms because they serve as the only known means of translating genetic information into cellular proteins, the main structural and catalytic elements of life. A clear manifestation of this importance is the observation that all cells have ribosomes.

Bacterial ribosomes contain three distinct RNA molecules which, at least in *Escherichia coli,* are referred to as 5S, 16S and 23S rRNAs. In eukaryotic organisms, there are four distinct rRNA species, generally referred to as 5S, 18S, 28S, and 58S. These names historically are related to the size of the RNA molecules, as determined by their sedimentation rate. In actuality, however, ribosomal RNA molecules vary substantially in size between organisms. Nonetheless, 5S, 18S, 28S, and 5.8S rRNA are commonly used as generic names for the homologous RNA molecules in any eukaryote, and this convention will be continued herein.

As used herein, probe(s) refer to synthetic or biologically produced nucleic acids (DNA or RNA) which, by design or selection, contain specific nucleotide sequences that alloy them to hybridize under defined predetermined stringencies, specifically (i.e., preferentially, see next paragraph) to target nucleic acid sequences. In addition to their hybridization properties, probes also may contain certain constituents that pertain to their proper or optimal functioning under particular assay conditions. For example, probes may be modified to improve their resistance to nuclease degradation (e.g. by end capping), to carry detection ligands (e.g. fluoroscien, 32-P, biotin, etc.), or to facilitate their capture onto a solid support (e.g., polydeoxyadenosine "tails"). Such modifications are elaborations on the basic probe function which is its ability to usefully discriminate between target and non-target organisms in a hybridization assay.

Hybridization traditionally is understood as the process by which, under predetermined reaction conditions, two partially or completely complementary strands of nucleic acid are allowed to come together in an antiparallel fashion (one oriented 5' to 3', the other 3' to 5') to form a double-stranded nucleic acid with specific and stable hydrogen bonds, following explicit rules pertaining to which nucleic acid bases may pair with one another. The high specificity of probes relies on the low statistical probability of unique sequences occurring at random as dictated by the multiplicative product of their individual probabilities. These concepts are yell understood by those skilled in the art.

The stringency of a particular set of hybridization conditions is determined by the base composition of the probe/target duplex, as well as by the level and geometry of mispairing between the two nucleic acids.

Stringency may also be governed by such reaction parameters as the concentration and type of ionic species present in the hybridization solution, the types and concentrations of denaturing agents present, and the temperature of hybridization. Generally, as hybridization conditions become more stringent, longer probes are preferred if stable hybrids are to be formed. As a corollary, the stringency of the conditions under which a hybridization is to take place (e.g., based on the type of assay to be performed) will dictate certain characteristics of the preferred probes to be employed. Such relationships are well understood and can be readily manipulated by those skilled in the art.

As a general matter, dependent upon probe length, such persons understand stringent conditions to mean approximately 35°–65° C. in a salt solution of approximately 0.9 molar. All references herein are fully incorporated by reference.

SUMMARY OF THE INVENTION

In accordance with the various principles and aspects of the present invention, there are provided nucleic acid probes and probe sets comprising deoxyribonucleic acid (DNA) or ribonucleic acid (RNA) sequences which hybridize, under specific conditions, to the ribosomal RNA molecules (rRNA), specifically 18S rRNA molecules, or rRNA genes (rDNA) of *Cryptococcus neoformans* but which do not hybridize, under the same conditions, to the rRNA or rDNA of other fungi or bacteria which may be present in test samples. The probes of the present invention now permit the development of a valuable nucleic acid hybridization assay for the specific detection of cryptococcosis or its etiological agent. This assay may advantageously be used to test clinical samples of blood, urine, cerebrospinal fluid, skin biopsy, saliva, synovial fluid, sputum, bronchial wash, bronchial lavage, or other tissue or fluid samples from human patients or veterinary subjects. The probes also provide the basis for epidemiological evaluation of pigeon droppings.

Nucleic acid hybridization based assays have been discovered to impart enhanced performance capabilities with respect to most currently available, microbiological or immunological methods for detection of bacteria in test samples, generally including:

a) increased sensitivity; i.e., the ability to detect said yeast in a given sample more frequently;

b) potentially significant reductions in assay cost due to the use of inexpensive reagents and reduced labor;

c) accurate identification of even biochemically unusual strains of the target organism, or isolates with dramatically different antigenic properties;

d) direct assay for the presence of the yeast and consequent potential to quantify the etiological agents;

e) direct testing alloys the monitoring of the efficacy of an antifungal regime; and f) potentially significant reductions in the exposure of laboratory technologists to bodily fluid specimens harboring infectious agents.

It has been discovered that other advantages incurred by directing the probes of the present invention against rRNA include the fact that the rRNAs detected constitute a significant component of cellular mass. Although estimates of cellular ribosome content vary, actively growing *Cryptococcus neoformans* may contain upwards of 100,000 ribosomes per cell, and therefore 100,000 copies of each of the rRNAs (present in a 1:1:1:1 stoichiometry in ribosomes). In contrast, other potential cellular target molecules such as genes or RNA transcripts thereof, are less ideal since they are present in much lover abundance. A further unexpected advantage is that the rRNAs (and the genes specifying them) appear not to be subject to lateral transfer between contemporary organisms. Thus, the rRNA primary structure provides an organism-specific molecular target, rather than a gene-specific target as would likely be the case, for example of a plasmid-borne gene or product thereof which may be subject to lateral transmission between contemporary organisms.

The discovery that probes could be generated with the extraordinary inclusivity and exclusivity characteristics of those of the present invention with respect to the detection of the etiological agent of cryptococcosis, *Cryptococcus neoformans,* was unpredictable and unexpected.

BRIEF DESCRIPTION OF THE TABLE AND FIGURE

Further understanding of the principles and aspects of the present invention may be made by reference to the table wherein:

Table displays the hybridization behavior of three probes toward a panel of clinically representative Cryptococcus species and other fungi, human, wheat, stool RNA, and two ubiquitous bacterial species. All species on the panel are represented by 100 ng of purified, denatured RNA. Probes were 32-Phosphorous labelled, hybridized to panels under standard conditions, and autoradiographically evaluated. "+" represents strong hybridization signal after three hours exposure, "+—" is a weak signal, "+—" is virtually absent, and "–" indicates no hybridization of probe to target.

And wherein the FIGURE schematically represents a dual probe capture/detector assay.

DETAILED DESCRIPTION OF THE INVENTION AND BEST MODE

Probe Development Strategy

Figure 1:
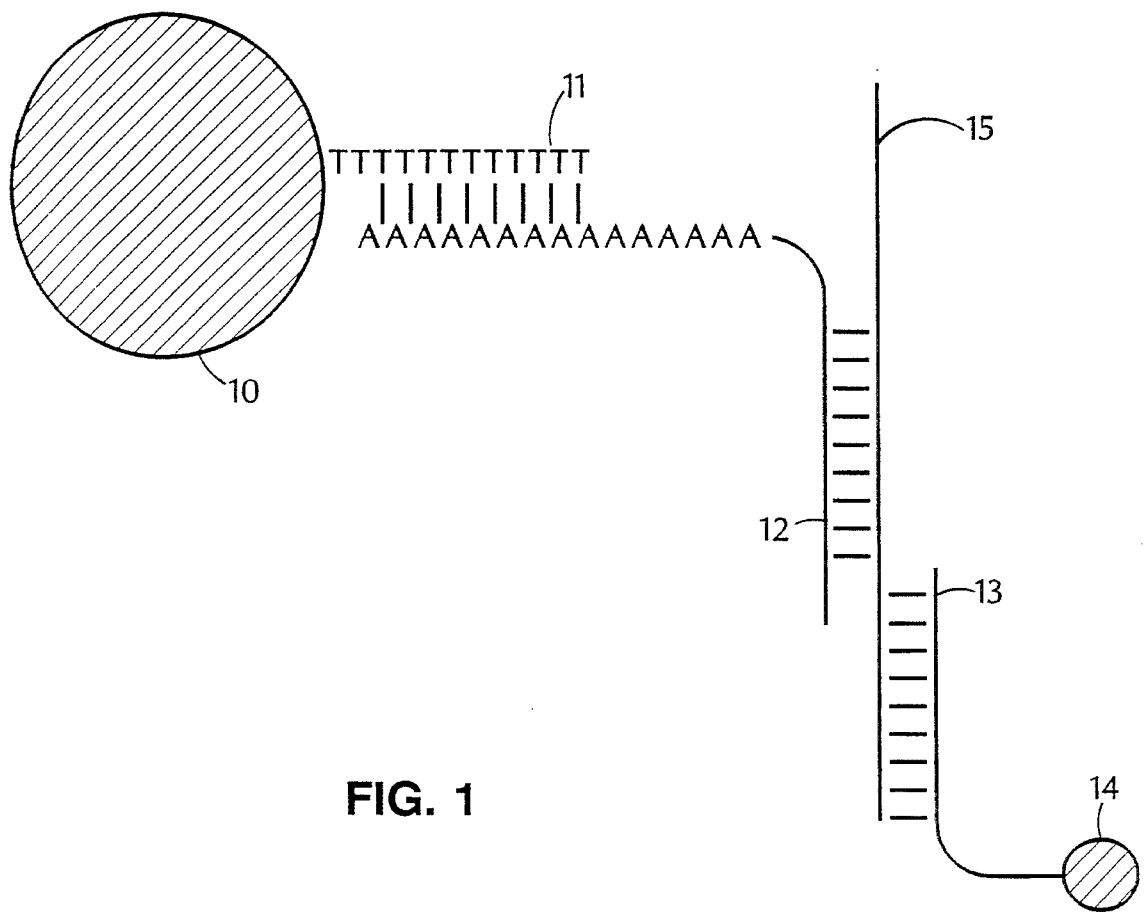

The 18S rRNA sequence from the type strain of *Cryptococcus neoformans,* American Type Culture Collection strain number 32045 was determined by conventional standard laboratory methods and compared to sequences of other fungal 18S rRNAs. This approach narrowed considerably the search for worthwhile target sequences within the 18S rRNA. Interesting target seqeunces were defined as those containing clustered mismatches when compared to other published and proprietary fungal ribosomal sequences. Probes were designed so as to optimize the distribution of mismatches of probe hybridizing to other sequences. Additional evaluation of 18S rRNA sequences from other significant meningitis-causing organisms, including bacteria, also contributed to ultimate probe design.

Physical Description of the Probes

The probe selection strategy yielded three probes useful for identifying *Cryptococcus neoformans* in samples and include the following preferred oligonucleotide probes:

PROBE 1679: 5'-GAGCATACAGGACCACCAGGAG-GTAAGGTT-3'

PROBE 1686: 5'-TTGATCAGCTTCTCAGC-CAAGGGGTGCCGTT-3'

PROBE 1687: 5'-CCCAGTCAGAGATTGACGTGGGC-CGATCCCT-3'

Two additional oligonucleotides useful with the foregoing include:

PROBE/PRIMER 936: 5'-CCGAATTCGTCGACAAC-CTGGTTGATCCTGCCAGT-3'

PROBE/PRIMER 935: 5'-CCCGGGATCCAAGCT-TGATCCTTCTGCAGGTTCACCTAC-3'

Probe/Primer 936 is designed to hybridize to the 18S rDNA gene strand complimentary to the cryptococcal 18S rRNA.

Oligonucleotides 935 and 936 are designed for use in assays employing amplification, by the polymerase chain reaction method, of almost the entire 18S rRNA gene (EDNA) of *Cryptococcus neoformans* and relatives. Additional discussion regarding these probes may be had by reference to commonly assigned, copending U.S. Ser. No. 07/780,800, abandoned of Weisburg et al. (Docket No. GT2-5.0, entitled "Nucleic Acid Probes and Methods for Detecting Fungi") and to Example 4.

EXAMPLE 1 Dot-Blot Analysis of Probe Hybridization Behavior

Dot-blot analysis, in accordance with veil known procedures, involves immobilizing a nucleic acid or a population of nucleic acids on a filter such as nitrocellulose, nylon, or other derivatized membranes which can readily be obtained commercially, specifically for this purpose. Either DNA or RNA can be easily immobilized on such a filter and subsequently can be probed or tested for hybridization under any of a variety of conditions (i.e., stringencies) with nucleotide sequences or probes of interest. Under stringent conditions, probes whose nucleotide sequences have greater complementarity to the target will exhibit a higher level of hybridization than probes containing less complementarity.

Probes 1679, 1686, and 1687 were tested in a dot-blot format. One hundred nanograms of target RNA, purified by phenol extraction and centrifugation through cesium triflouroacetate gradients, was denatured and spotted on a nylon membrane. Probes were isotopically labelled with the addition of a 32-Phosphorous moiety to the 5' end of the oligonucleotide. Hybridization of probes occurred, at a temperature of 60° C. in the presence of 1.08M sodium chloride, 60 mM sodium phosphate, and 6 mM ethylenediamine tetraacetic acid, pH 7.4. Unhybridized probe was removed by washing at a salt concentration one-third of the hybridization condition. The filters were exposed to X-ray film and the intensity of hybridization signals was evaluated after three hours of exposure.

Probes 1679 and 1687 hybridize to all representatives of four serotypes of *Cryptococcus neoformans* without cross-reacting with any of the other Cryptococcus species. (The sole exclusivity problem with Probes 1679 or 1687 is a very weak signal from *Trichosporon beigelii*.) Probe 1686 could be used, by varying stringency conditions, to distinguish serotype A from the other three serotypes.

EXAMPLE 2: Dual Probe Hybridization

In actual practice, many applications of these probes would employ a pair of probes being used simultaneously in a "sandwich" hybridization scheme of "capture" probe and "detector" probe as shown in FIG. 2. The capture probe[12] ideally would be a bifunctional polynucleotide manufactured by adding a homopolymeric 3' tail to a probe with high target specificity. The tail would, in turn, hybridize to the complimentary homopolymer[11] on a solid surface[10], such as a glass bead or a filter disc. Hybridization of the capture probe[12] to its target[15] in this case *Cryptococcus neoformans* 18S rRNA would complex the target[15] with the solid support[10]. The detector probe[13], advantageously also with some degree of specificity, would be part of a preferred detection scheme relying on radioactivity, fluorescence, chemiluminescence, color, etc. (detection moiety[14]) which would report the presence of the entire hybridization complex.

For specific detection of the infectious agent of cryptococcosis, *Cryptococcus neoformans*, a combination of probes 1679 and 1687, for example, can be employed with one derivatized as detector, end the other as a capture probe.

EXAMPLE 3 Clinical Diagnosis of Cryptococcosis from Human Blood, Sputum, or Cerebrospinal Fluid Sample The clinical sample is ideally processed so as to yield total nucleic acid content such as by sonication, vortexing with glass beads, detergent lysis using an agent such as SDS or by chemical treatment. Alternatively, yeast cells may be partially purified by, for example, the DuPont Isolator System, followed by cell lysis. The sample, containing disrupted Cryptococcal cells is then incubated in the presence of capture probe, detector probe, and ideally magnetic particle beads which have been derivatized with oligo-Thymidine (see also Example 2) in a chaotropic buffer such as guanidinium isothiocyanate described by Gillespie et al, U.S. Ser. No. 299,150, abandoned.

If *Cryptococcus neoformans* 18S rRNA target molecules are present, a Bead+Capture Probe+Target+Detector Probe hybridization complex is formed. The exterior presence of a magnet near the bottom of the reaction tube rill cause the magnetic particle-hybridization complex to adhere to the interior side of the tube thereby advantageously enabling removal of the unreacted components such as sample matrix, unbound probe, etc. Repeated rehydration and denaturation of the bead-probe-target complex would enable significant background reduction (as more fully described in Collins, et al, U.S. Ser. No. 922,155, abandoned, EPA 87309308.2). In this example, final detection could entail spotting the beads on membrane and assaying by autoradiography.

EXAMPLE 4 Clinical Diagnosis of Cryptococcosis from Human Sample Employing Polymerase Chain Reaction Amplification Sample processing such as provided in Example 3 is ideally designed so as to yield DNA. The DNA is further treated to make it single stranded (e.g. by melting) in preparation for polymerase chain reaction ("PCR") amplification. Probe/Primer 936 and Probe/Primer 935 are employed in conjunction with the clinical sample in the standard PCR procedures. Resultant material may then be suitably assayed utilizing the "sandwich" hybridization procedures of Example 2 with any of the probes described herein. The polymerase chain reaction can, itself, be made highly specific by employing Probe/Primer 936 in conjunction with, for example, Probe 1687. Detection is advantageously accomplished using Probe 1679 for capture and Probe 1687 for detection.

EXAMPLE 5 In situ Hybridization as a Cytological Stain

The probes of the present invention can also be advantageously employed as a cytological staining reagent. For example, a sputum sample is applied to a microscope slide. After appropriate fixation and lysis, hybridization with the probes of the present invention is carried out in situ. In this manner, *Cryptococcus neoformans* cells could be visualized in a specimen by fluorescently labelling Probes 1679 or 1687 and examining the slide under a fluorescent microscope.

EXAMPLE 6 Environmental Sample Evaluation for Epidemiological Study

Using the probes and hybridization scheme of Example 2, the environmental reservoir of *Cryptococcus neoformans*, droppings of the common pigeon, *Columba livia*, could be evaluated for infectious potential.

EXAMPLE 7 Confirmation of Cryptococcal Fungemia Following Culture

Following a standard cultivation step utilizing the Barter, Roche Septi-Chek, or DuPont Isolator, colony or liquid culture is tested for *Cryptococcus neoformans* employing Probes 1679 and 1687 in the procedures described in Example 2. Of great advantage is that pure culture is not necessary.

It will be readily appreciated by those skilled in the art that various modifications to the procedures or probes set forth herein may be made without departing from either the spirit or scope of the present invention. In particular, when modifications of the probes such as by deleting one or two end nucleotides with accompanying adjustments in hybridization conditions are to be deemed equivalent.

TABLE

DOTBLOT HYBRIDIZATION DATA

| NAME/STRAIN | | PROBE | | |
|---|---|---|---|---|
| | | 1679 | 1686 | 1687 |
| *Alternaria alternata* | 13963 | − | − | − |
| *Agaricus brunnescens* | n5829 | − | + | − |
| *Aspergillus flavus* | 10124 | − | − | − |
| *Aspergillus fumigatus* | 36607 | − | − | − |
| *Aspergillus nidulans* | 10074 | − | − | − |
| *Aspergillus niger* | 16888 | − | − | − |
| *Aspergillus parasiticus* | 15517 | − | − | − |
| *Aspergillus terreus* | 46941 | − | − | − |
| *Aspergillus versicolor* | 95776 | − | − | − |
| *Blastomyces dermatitidis* | 60916 | − | − | − |
| *Byssochlamys fulva* | 10099 | − | − | − |
| *Candida albicans* | 11006 | − | − | − |
| *Candida albicans* | 14053 | − | − | − |
| *Candida albicans* | 18804 | − | − | − |
| *Candida albicans* | 24433 | − | − | − |
| *Candida albicans* | 36232 | − | − | − |
| *Candida albicans* | 60193 | − | − | − |
| *Candida guilliermondii* | 6260 | − | − | − |
| *Candida kefyr* | 4135 | − | − | − |
| *Candida kefyr* | 46764 | − | − | − |
| *Candida krusei* | 6258 | − | − | − |
| *Candida lusitaniae* | 42720 | − | − | − |
| *Candida parapsilosis* | 22019 | − | − | − |
| *Candida rugosa* | 58964 | − | − | − |
| *Candida tropicalis* | 750 | − | − | − |
| *Candida tropicalis* | 13803 | − | − | − |
| *Candida tropicalis* | 42678 | − | − | − |
| *Candida utilis* | 9226 | − | − | − |
| *Candida viswanathii* | 22981 | − | − | − |
| *Chrysosporium keratinophilum* | 14803 | − | − | − |
| *Cladosporium castellani* | 24788 | − | − | − |
| *Cryptococcus neoformans* | 14116 | + | +− | + |
| *Cryptococcus neoformans* | 32045 | + | + | + |
| *Cyathus stercoreus* | n6473 | − | +− | − |
| *Entomophthora virulenta* | 14207 | − | − | − |
| *Epidermophyton floccosum* | 52066 | − | − | − |
| *Filobasidiella neoformans* | 6352 | + | +− | + |
| *Fusarium oxysporum* | 16322 | − | − | − |
| *Hansenula polymorpha* | 34438 | − | − | − |
| *Histoplasma capsulatum* | 12700 | − | − | − |
| *Geotrichum candidum* | 34614 | − | − | − |
| *Lipomyces starkeyi* | n11557 | − | − | − |
| *Metschnikowia bicuspidata* | 22297 | − | − | − |
| *Microsporum racemosum* | 38556 | − | − | − |
| *Morchella crassipes* | 18408 | − | − | − |
| *Mucor rouxii* | 24905 | − | − | − |
| *Neurospora crassa* | 14692 | − | − | − |
| *Neurospora sitophila* | 36935 | − | − | − |
| *Paracoccidioides brasiliensis* | 48093 | − | − | − |

TABLE-continued

DOTBLOT HYBRIDIZATION DATA

| NAME/STRAIN | | PROBE | | |
|---|---|---|---|---|
| | | 1679 | 1686 | 1687 |
| *Penicillium chrysogenum* | 10106 | − | − | − |
| *Penicillium digitatum* | 48113 | − | − | − |
| *Penicillium notatum* | 9179 | − | − | − |
| *Phycomyces blakesleeanus* | n1464 | − | − | − |
| *Pityrosporum ovale* | 14521 | − | − | − |
| *Pseudallescheria boydii* | 28169 | − | − | − |
| *Rhizopus oligosporus* | 22959 | − | − | − |
| *Rhodosporidium toruloides* | 10788 | − | − | − |
| *Rhodotorula rubra* | 9449 | − | − | − |
| *Saccharomyces cerevisiae* | 18824 | − | − | − |
| *Saccharomycodes ludwigii* | n12792 | − | − | − |
| *Schizosaccharomyces octosporus* | 4206 | − | − | − |
| *Sporothrix schenkii* | 14284 | − | − | − |
| *Taphrina deformans* | nT857 | − | − | − |
| *Torulopsis glabrata* | 2001 | − | − | − |
| *Tremella mesenterica* | 42219 | − | +− | − |
| *Trichophyton mentagrophytes* | 28185 | − | − | − |
| *Trichophyton rubrum* | 28188 | − | − | − |
| *Trichosporon beigelii* | 28592 | − | − | +− |
| *Trichosporon capitatum* | 10663 | − | − | − |
| *Ustilago maydis* | j1402 | − | − | − |
| *Verticillium dahliae* | 16535 | − | − | − |
| *Yarrowia lipolytica* | 18942 | − | − | − |
| TOTAL (n = 72; 42 genera) EXCLUSIVITY | | | | |
| HUMAN/CaSKi | | | | |
| *Staphylococcus aureus* | GT2047 | − | − | − |
| *Escherichia coli* | 12036 | − | − | − |
| Stool RNA | | − | − | − |
| Wheat germ RNA | | − | − | − |
| *Candida albicans*(n = 47) | | | | |
| 151-87 | | − | − | − |
| 184-87 | | − | − | − |
| 192-87 | | − | − | − |
| 738-88 | | − | − | − |
| 784-88 | | − | − | − |
| 819-88 | | − | − | − |
| 854-88 | | − | − | − |
| 864-88 | | − | − | − |
| 875-88 | | − | − | − |
| 876-88 | | − | − | − |
| 889-88 | | − | − | − |
| 892-88 | | − | − | − |
| 896-88 | | − | − | − |
| 901-88 | | − | − | − |
| 903-88 | | − | − | − |
| 904-88 | | − | − | − |
| 917-88 | | − | − | − |
| 921-88 | | − | − | − |
| 925-88 | | − | − | − |
| 926-88 | | − | − | − |
| 939-88 | | − | − | − |
| 943-88 | | − | − | − |
| 946-88 | | − | − | − |
| 966-88 | | − | − | − |
| 993-88 | | − | − | − |
| 161-87 | | − | − | − |
| 162-87 | | − | − | − |
| 190-87 | | − | − | − |
| 203-87 | | − | − | − |
| 207-87 | | − | − | − |
| 223-87 | | − | − | − |
| 227-87 | | − | − | − |
| 258-87 | | − | − | − |
| 262-87 | | − | − | − |
| 266-87 | | − | − | − |
| 291-87 | | − | − | − |
| 296-87 | | − | − | − |
| 307-87 | | − | − | − |
| 308-87 | | − | − | − |

TABLE-continued
DOTBLOT HYBRIDIZATION DATA

| NAME/STRAIN | PROBE | | |
|---|---|---|---|
| | 1679 | 1686 | 1687 |
| 326-87 | − | − | − |
| 342-87 | − | − | − |
| 662-87 | − | − | − |
| 996-87 | − | − | − |
| 984-88 | − | − | − |
| 1008-88 | − | − | − |
| 1018-88 | − | − | − |
| *Candida quilliermondii*(n = 4) | | | |
| 1055-86 | − | − | − |
| 350-87 | − | − | − |
| 715-88 | − | − | − |
| 974-88 | − | − | − |
| *Candida krusei*(n = 4) | | | |
| 46-87 | − | − | − |
| 528-87 | − | − | − |
| 842-88 | − | − | − |
| 939-88 | − | − | − |
| *Candida (Yarrowia) lipolytica*(n = 4) | | | |
| 0565-84 | − | − | − |
| 1034-86 | − | − | − |
| 1250-85 | − | − | − |
| 453-87 | − | − | − |
| *Candida lusitaniae*(n = 4) | | | |
| 1215-85 | − | − | − |
| 1216-85 | − | − | − |
| 403-87 | − | − | − |
| 964-88 | − | − | − |
| Candida parapsilosis(n = 8) | | | |
| 175-87 | − | − | − |
| 176-87 | − | − | − |
| 491-87 | − | − | − |
| 492-87 | − | − | − |
| 746-88 | − | − | − |
| 754-88 | − | − | − |
| 828-88 | − | − | − |
| 951-88 | − | − | − |
| *Candida (kefyr) pseudotropicalis*(n = 4) | | | |
| 0914-86 | − | − | − |
| 1001-88 | − | − | − |
| 1028-86 | − | − | − |
| 999-88 | − | − | − |
| Candida tropicalis(n = 11) | | | |
| 484-87 | − | − | − |
| 784-88 | − | − | − |
| 802-88 | − | − | − |
| 846-88 | − | − | − |
| 997-88 | − | − | − |
| 999-88 | − | − | − |
| 150-87 | − | − | − |
| 210-87 | − | − | − |
| 224-87 | − | − | − |
| 319-87 | − | − | − |
| 573-87 | − | − | − |
| Torulopsis glabrata(n = 13) | | | |
| 233-87 | − | − | − |
| 260-87 | − | − | − |
| 275-87 | − | − | − |
| 288-87 | − | − | − |
| 334-87 | − | − | − |
| 359-87 | − | − | − |
| 373-87 | − | − | − |
| 506-87 | − | − | − |
| 562-87 | − | − | − |
| 573-87 | − | − | − |
| 701-87 | − | − | − |

TABLE-continued
DOTBLOT HYBRIDIZATION DATA

| NAME/STRAIN | PROBE | | |
|---|---|---|---|
| | 1679 | 1686 | 1687 |
| 901-88 | − | − | − |
| 903-88 | − | − | − |
| Cryptococcus albidus(n = 5) | | | |
| 83-0085 | − | +− | − |
| 85-0707 | − | − | − |
| 85-0808 | − | +− | − |
| 85-1452 | − | − | − |
| 88-1047 | − | − | − |
| Cryptococcus laurentii(n = 3) | | | |
| 82-0600 | − | +− | − |
| 87-0657 | − | + | − |
| 88-0010 | − | + | − |
| Cryptococcus neoformans A(n = 4) | | | |
| 151 | + | +− | + |
| 159 | + | +− | + |
| 160 | + | +− | + |
| 161 | + | +− | + |
| Cryptococcus neoformans B(n = 5) | | | |
| 182 | + | +− | + |
| 184 | + | + | + |
| B3174a | + | + | + |
| B3268b | + | +− | + |
| B3271a | + | + | + |
| Cryptococcus neoformans C(n = 5) | | | |
| 298 | + | + | + |
| B3185a | + | +− | + |
| B3186a | + | + | + |
| B3267b | + | +− | + |
| CP110 | + | + | + |
| Cryptococcus neoformans D(n = 5) | | | |
| 161 | + | +− | + |
| 165C | + | + | + |
| 166 | + | + | + |
| 167 | + | +− | + |
| 168 | + | +− | + |

What is claimed is:

1. A purified nucleic acid probe which hybridizes under predetermined stringency conditions to 18S rRNA or rDNA of *Cryptococcus neoformans* to form a stable hybridization complex, but does not form a stable complex with the rRNA or rDNA of non-Cryptococcus organisms under said conditions, wherein said probe consists of a nucleotide sequence fully complementary or identical to about 30 consecutive nucleotides within a nucleotide sequence of any one of probes 1679 or 1687.

2. A nucleic acid probe of claim 1, wherein said probe is identical or fully complementary to any one of probes 1679 or 1687.

3. A set of nucleic acid probes comprising at least two probes, wherein at least one of said probes is a probe of claim 1.

4. A set of nucleic acid probes of claim 3, wherein said set comprises probe 1686 and at least one of probes 1679 and 1687.

5. A method for detecting the presence of *Cryptococcus neoformans* in a sample comprising a) contacting the sample with at least one purified nucleic acid probe of claim 1;

b) imposing said predetermined stringency conditions on said sample and said nucleic acid probe to allow said probe to hybridize to 18S rRNA or rDNA of *Cryptococcus neoformans,* if present in the sample, to form a stable hybridization complex, said conditions not allowing said nucleic acid probe to form a stable hybridization complex with the rRNA or rDNA of non-Cryptococcus organisms; and c) detecting said hybridization complex as an indication of the presence of *Cryptococcus neoformans* in said sample.

6. A method of claim 5, wherein said probe is identical or fully complementary to any one of probes 1679 or 1687.

7. A method of claim 5, wherein one or both of probe/primer 936 and probe/primer 935 are used and said detecting step further comprises contacting the sample with a second nucleic acid probe, wherein said second probe is identical or fully complementary to any one of probes 1679 or 1687.

8. A method of claim 5, further comprising the step of amplifying cryptococcal 18S rRNA or rDNA sequences by polymerase chain reaction before said contacting step.

* * * * *

UNITED STATES PATENT AND TRADEMARK OFFICE
CERTIFICATE OF CORRECTION

PATENT NO. : 5,464,743

DATED : November 7, 1995

INVENTOR(S) : William G. Weisburg et al.

It is certified that error appears in the above-indentified patent and that said Letters Patent is hereby corrected as shown below:

Col. 1, line 7, insert --now abandoned-- after "1989".
     line 40, "rill" should be --will--.

Col. 2, line 1, "sake" should be --make--.
     line 29, "58S" should be --5.8S--.
     line 39, "alloy" should be --allow--.
     line 63, "yell" should be --well--.

Col. 4, line 33, "+-" 1st occurence should be -- + - --.
              "+-" 2nd occurence should be -- + --.

Col. 5, line 8, "complimentary" should be --complementary--.
     line 63, "complimentary" should be --complementary--.
     line 22, "veil" should be --well--.

UNITED STATES PATENT AND TRADEMARK OFFICE
CERTIFICATE OF CORRECTION

PATENT NO. : 5,464,743
DATED : November 7, 1995
INVENTOR(S) : William G. Weisburg et al.

It is certified that error appears in the above-indentified patent and that said Letters Patent is hereby corrected as shown below:

Col. 6, line 8, "end" should be --and--.
     line 26, "rill" should be --will--.

Col. 7, line 6, "Barter" should be --Bactec--.

Col. 10, under 1686 in the Table, all "+--" should be -- +-- -- and all "+-" should be -- + --.

Signed and Sealed this

Fourteenth Day of October, 1997

Attest:

BRUCE LEHMAN

Attesting Officer     Commissioner of Patents and Trademarks